US011389339B2

(12) United States Patent
Schiffer

(10) Patent No.: US 11,389,339 B2
(45) Date of Patent: Jul. 19, 2022

(54) DETERMINING A PRESENCE OF AUTO-FLUORESCENT BIOLOGICAL SUBSTANCES THROUGH AN ARTICLE

(71) Applicant: Verily Life Sciences LLC, South San Francisco, CA (US)

(72) Inventor: Brian Schiffer, San Francisco, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 447 days.

(21) Appl. No.: 16/542,898

(22) Filed: Aug. 16, 2019

(65) Prior Publication Data
US 2021/0045934 A1    Feb. 18, 2021

(51) Int. Cl.
A61F 13/42    (2006.01)
G01V 8/12    (2006.01)
G01N 21/64    (2006.01)
A61F 13/84    (2006.01)

(52) U.S. Cl.
CPC ............. *A61F 13/42* (2013.01); *G01N 21/64* (2013.01); *G01N 21/6428* (2013.01); *G01N 21/6486* (2013.01); *G01V 8/12* (2013.01); *A61F 2013/8491* (2013.01); *G01N 2021/6421* (2013.01)

(58) Field of Classification Search
CPC . A61F 13/42; A61F 2013/8491; G01N 21/64; G01N 21/6428; G01N 21/6486; G01N 2021/6421; G01V 8/12
See application file for complete search history.

(56) References Cited

U.S. PATENT DOCUMENTS

| 4,315,159 | A | 2/1982 | Niwa et al. |
| 4,336,459 | A | 6/1982 | Fay |
| 5,520,303 | A | 5/1996 | Bernstein et al. |
| 5,821,546 | A * | 10/1998 | Xiao ............... G01N 21/6486 250/459.1 |
| 5,895,920 | A | 4/1999 | Carlsson |
| 6,094,274 | A | 7/2000 | Yokoi |
| 6,603,126 | B2 | 8/2003 | Yamada et al. |
| 2003/0230728 | A1 | 12/2003 | Dai et al. |
| 2008/0265177 | A1 | 10/2008 | Connally et al. |

(Continued)

OTHER PUBLICATIONS

International Application No. PCT/US2020/042022, International Search Report and Written Opinion dated Oct. 15, 2020, 7 pages.
(Continued)

*Primary Examiner* — David P Porta
*Assistant Examiner* — Meenakshi S Sahu
(74) *Attorney, Agent, or Firm* — Kilpatrick Townsend & Stockton LLP

(57) ABSTRACT

Techniques are disclosed for detecting a presence of a biological substance through an article such as a diaper. For example, a detection system causes a light source to transmit light through the article. The light includes a peak wavelength that corresponds to an excitation wavelength of a biological substance that may be present in the article. The detection system detects a measurement of light intensity within a range of emission wavelengths of the biological substance. By comparing the measurement of light intensity to a threshold, the detection system identifies a presence of the biological substance on the article.

21 Claims, 7 Drawing Sheets

(56) References Cited

U.S. PATENT DOCUMENTS

| | | | |
|---|---|---|---|
| 2011/0117025 A1* | 5/2011 | Dacosta | A61B 5/01 435/5 |
| 2018/0024060 A1 | 1/2018 | Rochette et al. | |
| 2018/0185206 A1 | 7/2018 | Kuniavsky et al. | |

OTHER PUBLICATIONS

Getting the Best Out of Photodiode Detectors, Advanced Technology Development Group, Gray Cancer Institute 2005, 7 pages.

Ashby et al., Fluorescence of Dietary Porphyrins as a Basis for Real-Time Detection of Fecal Contamination on Meat, Journal of Agriculture and Food Chemistry, vol. 51, No. 11, May 21, 2003, pp. 3502-3507.

Brown, Advanced Planar Light Guide Solar Concentrators, The Institute of Optics, 2013, 199 pages.

Chen et al., Spectral Characteristics of Autofluorescence and Second Harmonic Generation from ex Vivo Human Skin Induced by Femtosecond Laser and Visible Lasers, Scanning, vol. 28, No. 6, Nov.-Dec. 2006, pp. 319-326.

Chisolm et al., Quantitative Urinary Coproporphyrin Excretion and its Relation to Edathamil Calcium Disodium Administration in Children with Acute Lead Intoxication, J. Clin. Invest., vol. 35, No. 10, Oct. 1956, pp. 1131-1138.

Cho et al., Potential Application of Fluorescence Imaging for Assessing Fecal Contamination of Soil and Compost Maturity, Applied Sciences, vol. 6, No. 9, Aug. 2016, 12 pages.

Croizat et al., Understanding the Delayed Fluorescence of Protoporphyrin IX to Quantify pO2 in Biological Tissues, Swiss Biomedical Photonics Network Annual Meeting, Dec. 2017, 2 pages.

Drobizhev et al., Photon Energy Upconversion in Porphyrins: One-Photon Hot-Band Absorption Versus Two-Photon Absorption, Chemical Physics Letters, vol. 370, Nos. 5-6, Mar. 21, 2003, pp. 690-699.

Haining et al., Rapid Porphyrin Screening of Urine, Stool, and Blood, Clin. Chem., vol. 15, No. 6, Jun. 1969, pp. 460-466.

Hall, Navigating the Lab-on-Chip Manufacturability Roadblock: Scalable, Low-cost Fluorescence Detection for Lab-on-Chip Instrumentation with Rapid-Prototyped Microfluidics, Electrical and Computer Engineering Theses, Apr. 30, 2018, 291 pages.

Iep, Low-Noise Preamplifier for Capacitive Sensors, Department of Electrical Engineering and Computer Science, Jun. 1995, 129 pages.

Jacob et al., Excretion Pattern of Faecal Coproporphyrin Isomers I-IV in Human Porphyrias, Eur. J. Clin. Chem. Clin. Biochem., vol. 33, No. 12, Dec. 1995, pp. 893-901.

Jope et al., Spectral Absorption and Fluorescence of Coproporphyrin Isomers I and III and the Melting-Points of Their Methyl Esters, Biochemical Journal, vol. 39, No. 3, Jan. 1, 1945, pp. 239-244.

Kantere et al., Anti-Stokes Fluorescence from Endogenously Formed Protoporphyrin IX—Implications for Clinical Multiphoton Diagnostics, Journal of Biophotonics, vol. 6, No. 5, May 2013, pp. 409-415.

Leahy et al., A Simple Method for the Separation and Quantification of Urinary Porphyrins, J. Clin. Pathol., vol. 35, No. 11, Nov. 1982, pp. 1232-1235.

Lefcourt et al., A Transportable Fluorescence Imagining System for Detecting Fecal Contaminants, Computers and Electronics in Agriculture, vol. 48, No. 1, Jul. 2005, pp. 63-74.

Localio et al., The Urinary/Fecal Coproporphyrin Ratio in Liver Disease, J. Clin. Invest., vol. 20, vol. 1, Jan. 1941, pp. 7-11.

Lowndes, Blood Interference in Fluorescence Spectrum—Experiment, Analysis and Comparison with Intraoperative Measurements on Brain Tumor, Institute of Technology, Linkoping University, Jul. 9, 2010, 42 pages.

Markwardt et al., 405 nm Versus 633 nm for Protoporphyrin IX Excitation in Fluorescence-Guided Stereotactic Biopsy of Brain Tumors, Journal of Biophotonics, vol. 9, No. 9, Sep. 2016, pp. 901-912.

Mik et al., Mitochondrial PO2 Measured by Delayed Fluorescence of Endogenous Protoporphyrin IX, Nature Methods, vol. 3, No. 11, Dec. 2006, 159 pages.

Minder et al., Age-Dependent Reference Values of Urinary Porphyrins in Children, Eur. J. Clin. Chem. Clin. Biochem., vol. 34, No. 5, May 1996, pp. 439-443.

Moore et al., Disorders of Porphyrin Metabolism, Springer Science & Business Media, 1998, 382 pages.

Oh et al., Detection of Fecal Contamination on Beef Meat Surfaces Using Handheld Fluorescence Imaging Device (HFID), Sensing for Agriculture and Food Quality and Safety VIII, Proceedings of SPIE, vol. 9864, May 17, 2016, pp. 986411-1-986411-6.

Roberts et al., Red-Light Excitation of Protoporphyrin IX Fluorescence for Subsurface Tumor Detection, J. Neurosurg., vol. 128, No. 6, Jun. 2018, pp. 1690-1697.

Rocchi et al., Coproporphyrin Excretion in Healthy Newborn Babies, Journal of Pediatric Gastroenterology and Nutrition, vol. 3, No. 3, Jun. 1984, pp. 402-407.

Tewari et al., Quantitative Estimation of Coproporphyrin III and Protoporphyrin IX from Their Mixture by Spectrofluorometry, Journal of Plant Biochemistry and Biotechnology, vol. 7, No. 1, Jan. 1998, pp. 43-46.

Tian, Anti-Stokes Fluorescence Spectroscopy and Imaging for Cutaneous Porphyrin Detection, Physics, A Thesis Submitted in Partial Fulfillment of the Requirements for the Degree of Master of Science in the Faculty of Graduate and Posdoctoral Studies (Physics), The University of British Columbia, Feb. 2015, 89 pages.

Troy et al., Quantitative Comparison of the Sensitivity of Detection of Fluorescent and Bioluminescent Reporters in Animal Models, Molecular Imaging, vol. 3, No. 1, Jan. 2004, pp. 9-23.

Tung et al., PDMS-Based Opto-Fluidic Micro Flow Cytometer with Two-Color, Multi-Angle Fluorescence Detection Capability Using PIN Photodiodes, Sensors and Actuators B Chemical, vol. 98, No. 2, Mar. 2004, pp. 356-367.

Vargas, Detection of Fecal Contamination on Cantaloupes and Strawberries Using Hyperspectral Fluorescence Imagery, Thesis submitted to the Faculty of the Graduate School of the University of Maryland, College Park, in Partial Fulfillment of the Requirements for the Degree of Master of Science, May 8, 2006, 82 pages.

Yamamoto et al., Local Temperature Variation Measurement by Anti-Stokes Luminescence in Attenuated Total Reflection Geometry, Optics Express, vol. 24, No. 17, Aug. 22, 2016, pp. 19026-19031.

* cited by examiner

DETERMINING A PRESENCE OF AUTO-FLUORESCENT BIOLOGICAL SUBSTANCES THROUGH AN ARTICLE

FIELD

The present application generally relates to detecting a presence of biological substances. More specifically, the present application relates to detecting a presence and amount of bodily exudate in an absorbent article such as a diaper.

BACKGROUND

Existing solutions for determining a presence of bodily exudate in an absorbent article (e.g., a diaper) can sometimes be unreliable. For example, solutions that rely on volatile organic compound (VOC) sensors are not always able to disambiguate detecting bodily exudate from other gases.

BRIEF DESCRIPTION OF THE DRAWINGS

Features, embodiments, and advantages of the present disclosure are better understood when the following Detailed Description is read with reference to the accompanying drawings.

Figure 1:
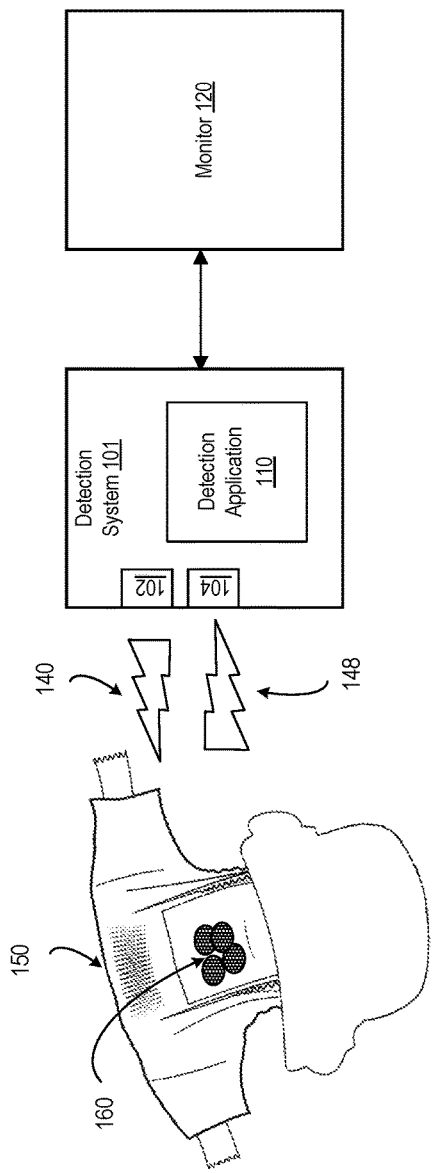
FIG. 1 depicts an example of a system for detecting a presence of a biological substance through an article, according to an aspect of the present disclosure.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

DETAILED DESCRIPTION

Disclosed solutions detect a presence of a substance by transmitting light through an article and measuring the returned light. Examples of articles are common disposable diapers, reusable cloth diapers, pantiliners, and adult diapers. Detectable substances include substances that fluoresce, for example biological structures such as chlorophyll, bilirubin, and porphyrin. Auto-fluorescence refers to a natural emission of light of certain substances in response to absorbing light (e.g., being stimulated with a light source). A molecule that exhibits fluorescence is called a fluorophore. Disclosed solutions can adjust a wavelength of the transmitted light to maximize fluorescence of the substance to be detected and to minimize an effect of other objects or substances fluorescing.

Disclosed solutions provide improvements relating to substance detection. For example, existing systems can sometimes be prone to erroneous measurements due to movement of a wearer of the absorbent article. In other cases, existing systems are unable to detect bodily exudate through a diaper. In contrast, disclosed solutions can detect a presence of a substance, e.g., bodily exudate, when a wearer of a diaper is moving.

A given fluorophore has a spectra of light at which it will absorb energy (some of which can be emitted) and a spectra that is emitted when it fluoresces and therefore may be characterized by an excitation curve and an emission curve. An excitation curve specific to a particular wavelength represents an amount of light emitted at the particular wavelength for a range of excitation wavelengths. For example, a particular chemical may emit light when excited by incoming light with a peak wavelength substantially at 600 or 650 nm, where the light emitted when excited at the peak wavelength of 600 nm is greater in intensity than the light emitted when excited at 650 nm. Therefore, the substance is said to absorb more energy at 600 nm than at 650 nm. An absorption curve for a given fluorophore represents the amount of energy that is absorbed for the particular wavelength. The absorption and excitation spectra are distinct, but often overlap.

An emission curve represents a range of wavelengths of light that are emitted for a given excitation wavelength. For example, an excitation curve for a chemical when stimulated with light with a peak wavelength of 420 nm may output a peak intensity at 630 nm and lower intensity light at other wavelengths. Typically, the most efficient excitation wavelength is close to the maximum peak of the absorption spectra. The difference between the peak excitation wavelength and the peak emission wavelength is called the Stokes' shift.

Disclosed solutions can adjust the wavelength(s) of emitted light to maximize a response of the substance to be detected and to minimize fluorescence of the article or any other substances. For example, an excitation wavelength with a lower absorption can sometimes result in a lower total intensity of emission, but there is not necessarily a direct linear correlation. This property can be leveraged to minimize background fluorescence by choosing an excitation spectra that includes peaks representing wavelengths that are poorly absorbed by any background material, including any undesired fluorophores, and high for the substance of interest. Alternatively, a ratio-based approach of sensing can be done by using multiple excitation wavelengths and measuring the difference in response.

In an example, light with one or more peak wavelengths is provided to an article. In turn, light emitted at one or more ranges of emission wavelengths can be detected. For example, disclosed solutions can excite a substance by providing light that includes two different peak wavelengths, each of which corresponds to an excitation wavelength of a biological substance that is to be detected. In an example, light with a first peak emission wavelength is first emitted, followed by a first measurement of the response, then light that includes a second peak emission wavelength is emitted, followed by a second measurement of a subsequent response. By analyzing an intensity of the measurements and/or a ratio of the measurements, disclosed solutions can detect a presence of a biological substance. Any number of excitation wavelengths and/or emission wavelengths can be used. The peak wavelengths can be identical or different. The peak wavelengths can overlap or not overlap, e.g., be mutually exclusive. Different combinations are possible.

Turning now to the Figures, FIG. 1 depicts an example of a system for detecting a presence of a biological substance through an article, according to an aspect of the present disclosure. FIG. 1 depicts sensing environment in which detection system 101 detects a presence or an absence of substance 160 on article 150 by emitting light 140, causing substance 160 (if present) to fluoresce, and measuring returned light 148. Returned light 148 can include light caused by the fluorescence of substance 160 (if present) and can include contributions from other sources. Based on a measurement of the returned light, detection system 101 identifies a presence or absence of substance 160. Examples of biological substances include bodily exudate such as feces and urine. Urine can be differentiated from feces based on urine and feces having different fluorescent emission peaks.

Monitor 120 can cause an alarm, such as an audible beep or other sound to be emitted, e.g., via a speaker, based on a threshold level of substance 160 being detected. Monitor 120 can also cause a transmission of an alert to another device, for example, operated by a caretaker. For example, monitor 120 can include a transmitter or transceiver capable of transmitting a radio signal to an external device. Monitor 120 can also log events, such as when bodily exudate is detected, to memory for later transmission to a caregiver. Detection system 101 can maintain a log for later transmission to monitor 120.

Detection system 101 can include one or more processors, light sources, photodetectors, wireless transmitters, analog-to-digital converters, or digital-to-analog converters (not depicted). Detection application 110 executes on detection system 101. Light source 102 can emit light at a particular wavelength or range of wavelengths. Examples of light sources include Light Emitting Diodes (LEDs), incandescent lights, and laser diodes. Photodetector 104 measures light at one or more wavelengths and provides a signal indicative of a strength of the measured light to detection application 110.

More particularly, photodetector 104 can be any device that can detect and measure light such as a photodiode, phototransistor, complementary metal-oxide-semiconductor (CMOS) image sensor, charge-coupled device (CCD) sensor, or a photo-resistor. Photodetector 104 receives light, including light reflected from article 150, whether ambient light or light emitted by light source 102, and generates sensor signals based on that received light. Photodetector 104 can detect a wide spectrum of light and output information that indicates the detected light. Photodetector 104 can provide three outputs e.g., a value that corresponds to red, another value for green, and another value for blue. The values of the triplet correspond to the amplitude of light at a range of wavelengths corresponding to a particular color. Therefore, a first value is proportional to an amplitude of red in the received light, a second value is proportional to an amplitude of green in the received light, and a third value is proportional to an amplitude of blue in the received light.

In some cases, detection application 110 can perform ambient light compensation by identifying contributions of any spectra of the measured light that is caused by ambient light, e.g., by obtaining a separate measurement of light without light source 102 activated. Even though ambient light can have different color spectra depending on the ambient light source(s) present, detection application 110 can electronically remove the contribution of such ambient light to light detected by the photodetector and accurately detect light from other sources, such as the light emitted by a fluorescent substance.

In a more specific example, detection application 110 causes light source 102 to emit light 140. In some cases, a pulse of light is emitted. A pulse can vary temporally, spectrally, and/or spatially. For example, a pulse can be a transmission of light for a specific amount of time, and/or include a specific range of wavelengths of light, and/or include light in one or more directions. In an example, a pulse of light may last for 500 milliseconds. But pulses of different duration can be used. For example, a duration can range from 100 milliseconds to five seconds. In turn, light 140 causes substance 160, if present in article 150, to fluoresce. Detection application 110 receives, from photodetector 104, an intensity of returned light 148. Any contributions of ambient light are removed from the measurement of returned light 148. The amount of returned light 148 at one or more particular wavelengths then indicates a presence and amount of substance 160. The intensity of returned light 148 can be compared to a threshold.

If the detected intensity is greater than a threshold, then detection application 110 determines that substance 160 is present. Otherwise, detection application 110 determines that substance 160 is absent. Upon the detection, detection application 110 can perform one or more actions. For example, detection application 110 can transmit a notification to monitor 120, cause an audible or visual alert, or create a log of the presence of absence of substance 160. An example of a process performed by detection application 110 to detect a presence or absence of a substance is discussed further with respect to FIG. 2.

Detection system 101 can be placed on or in an article. For example, detection system 101 can be integrated into a sensor package that is positioned on the article. The sensor package can also be inserted into a pocket or pouch inside the absorbent article. In this manner, the sensor package can be reused, for example, removed and inserted in a new article. The sensor package can be covered with a material or pouch that is washable or can be wiped. The sensor package can be inserted into an absorbent article or adhered to the inside of the absorbent article. Such a pocket or pouch can be hermetically sealed, for example, in transparent plastic that allows light to pass through. The sensor package can also be permanently attached into an absorbent article and discarded after a one-time use. The sensor package can also be adhered to the outside of the absorbent article via hook and loop or similar material.

Figure 2:
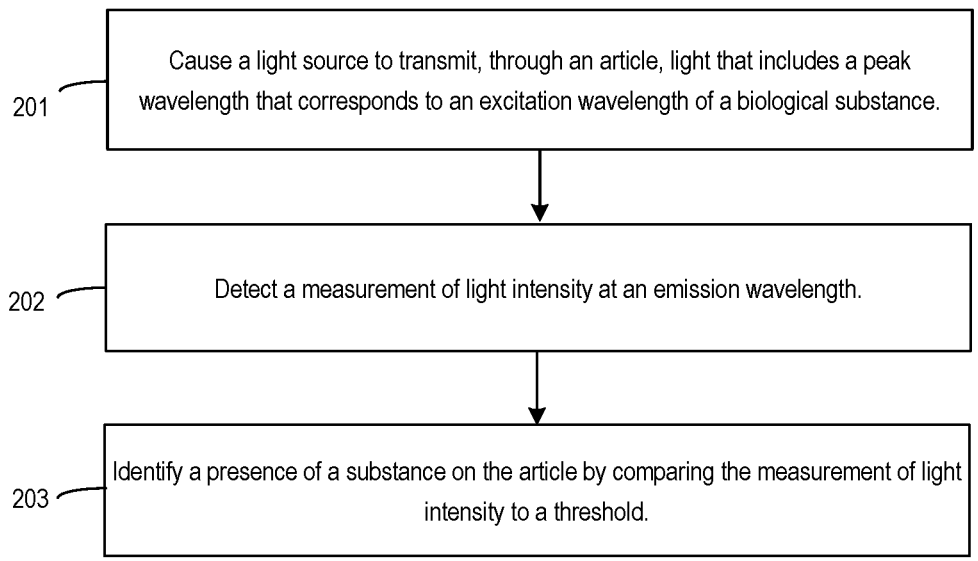
FIG. 2 illustrates an example of a process for detecting a presence of an auto-fluorescent biological substance, according to an aspect of the present disclosure.

FIG. 2 illustrates an example of a process 200 for detecting a presence of an auto-fluorescent biological substance, according to an aspect of the present disclosure. Process 200 can be implemented by detection system 101 or another system. Process 200 describes a simplified example using one excitation wavelength and one emission wavelength, but other configurations are possible. For example, the system described with respect to FIG. 4 can emit (and detect) multiple wavelengths of light.

At block 201, process 200 involves causing a light source to transmit, through an article, light that includes a peak wavelength that corresponds to an excitation wavelength of a biological substance. The peak wavelength can be selected based on the substance to be detected.

In an example, certain aspects detect a presence of bodily exudate. Bodily exudate can include fluorophores. For example, chlorophyll, secreted as a result of digesting vegetables can be present in bodily exudate and therefore can be tested. But for some human subjects, for example, babies, the detection of chlorophyll as a proxy for detecting a bowel movement can lead to false negatives because young infants do not eat solid foods. In contrast, porphyrins, which are also present in bowel movements as a byproduct of the body making hemoglobin, are a more reliable indicator that can be detected. Humans that are more efficient at manufacturing hemoglobin may emit lower quantities of porphyrins, but porphyrins are nevertheless still present in bodily exudate. Porphyrins have a high emission at wavelengths of 630 and 700 nm. Man-made structures such as diapers can also fluoresce, as well as other naturally occurring substances such as skin. Accordingly, contributions from other sources of fluorescence can be separated from a measurement of bodily exudate. In the case that chlorophyll and porphyrins are both present, the presence can be disambiguated due to the different response curves.

Figure 3:
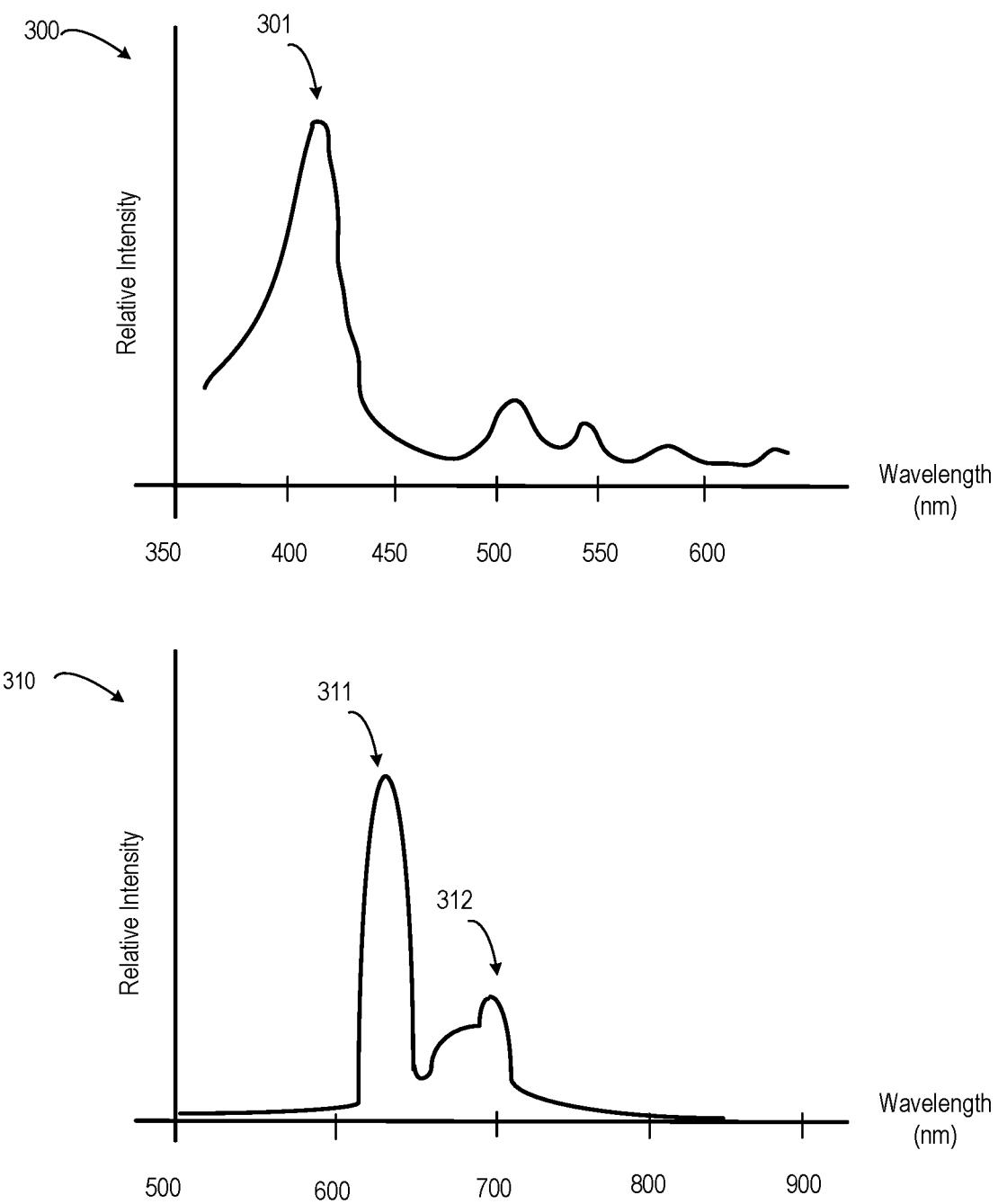
FIG. 3 depicts excitation and emission spectra for a substance, according to an aspect of the present disclosure.

FIG. 3 depicts excitation and emission curves for a biological substance. As depicted in the example of FIG. 3, the substance has an excitation curve as shown in graph 300 and an emission curve as shown in graph 310. The x-axis represents wavelengths of light and the y-axis represents a relative intensity. As depicted, the substance can be excited in various spectral regions ranging from violet light (405 nm) to near-infrared (around 700 nm). In particular, the excitation curve has peak 301 around 430 nm, which represents a wavelength at which a greater amount of energy is absorbed given a light source of equal amplitude relative to other wavelengths. The x-axis represents wavelengths of light and the y-axis represents a relative intensity. As depicted, the emission curve includes a peak 311 around 630 nm and second, smaller peak 312 around 700 nm.

Returning to FIG. 2, at block 202, process 200 involves detecting a measurement of light intensity at an emission wavelength (or a range of emission wavelengths). Continuing the example, detection application 110 detects returned light at 700 nm.

At block 203, process 200 involves identifying a presence of a substance on the article by comparing the measurement of light intensity to a threshold. For example, detection system 101 compares the amount of returned light at 630 nm to a threshold. Based on the returned light being higher than a threshold, detection system 101 can identify a presence of a substance on the article, indicating that bodily exudate is present on or in the article. If the amount of returned light is less than the threshold, then detection system 101 can identify an absence of the substance. This presence or absence can be transmitted to monitor 120.

Figure 4:
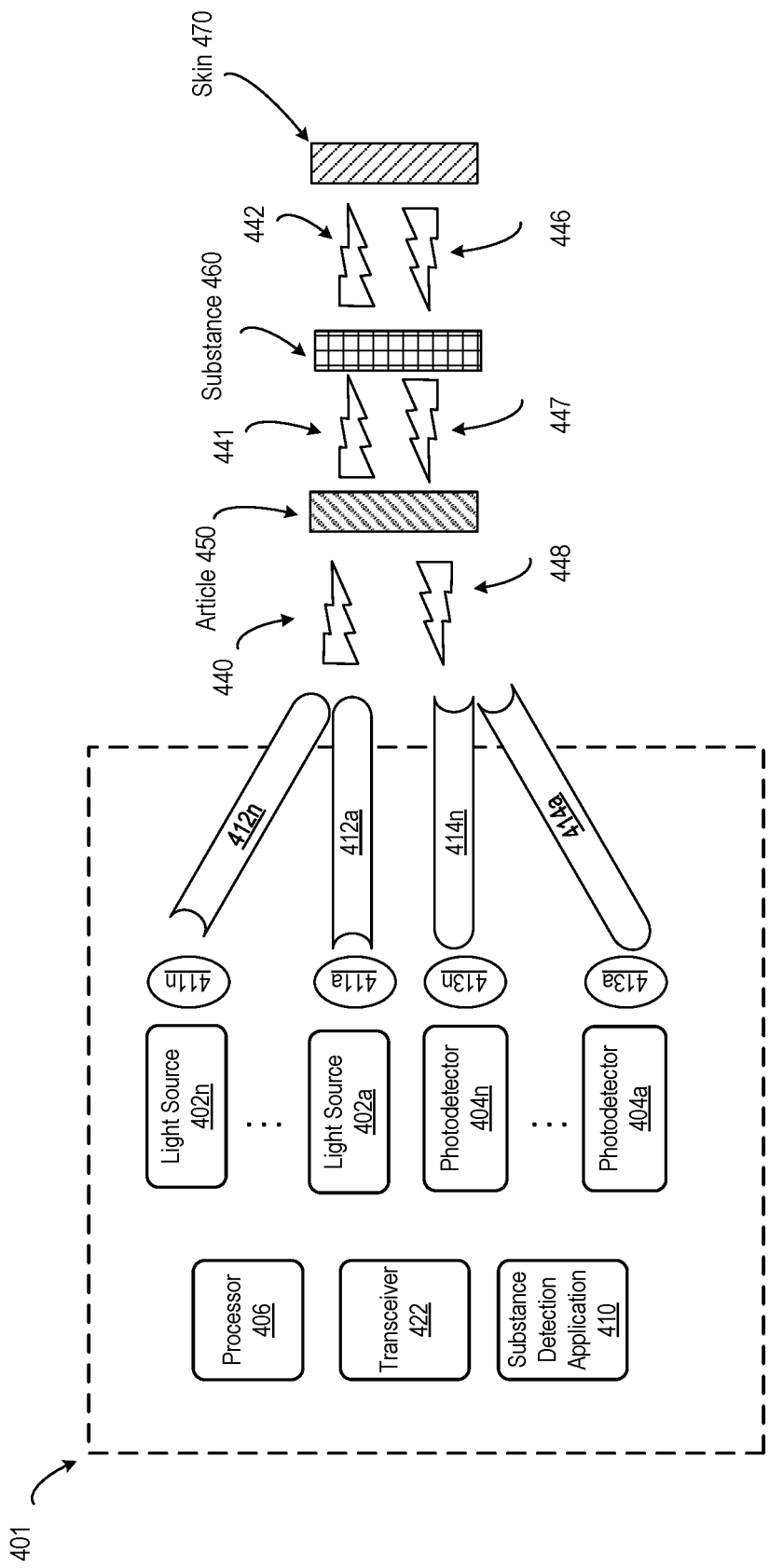
FIG. 4 depicts an additional example of a system for detecting a presence of a biological substance through an article, according to an aspect of the present disclosure.

FIG. 4 depicts an additional example of a system for detecting a presence of a biological substance through an article, according to an aspect of the present disclosure. FIG. 4 depicts sensing environment in which detection system 401 (which is an example of an implementation of detection system 101) detects a presence or an absence of substance 460 through article 450. Substance 460 can be any biological substance such as bodily exudate. Substance 460 can be on the surface of skin 470, which is the skin of the wearer of article 450, for example, an infant.

Detection system 401 also includes one or more processors 406 and transceivers 422. Examples of processors are microprocessors, microcontrollers, signal processors, and the like. Detection application 410 can execute on processor 406 and can cause light sources 402a-n to activate or deactivate, obtain measurements from photodetectors 404a-n, analyze signals representing received light, determine whether substance 160 is present, and communicate with external systems or devices. Transceiver 422 can be any wireless transceiver, for example, Bluetooth® or WiFi®. Detection system 401 can transmit to or receive data from an external monitor, device, system, or server.

For example, detection system 401 includes multiple light sources 402a-n and multiple photodetectors 404a-n. Using multiple light sources and detectors offers several benefits. Light source 402a-n can each be configured, for example, via an optical filter, to emit light at a specific range of wavelengths and can be activated simultaneously or in any sequence. Photodetectors 404a-n can be configured to detect light at specific wavelengths or ranges of wavelengths. Optical filters can be made of any suitable material such as plastic or glass.

Each of light source 402a-n includes a respective optical filter 411a-n. Each optical filter 411a-n can remove certain wavelengths of light, thereby restricting light emitted from the respective light source to a desired wavelength (e.g., an absorption wavelength of substance 460). Each optical filter 411a-n is connected to a waveguide 412a-n. The waveguides are optical waveguides that direct the emitted light to one or more output points, e.g., on the exterior of a sensing device.

The peak wavelengths used by light sources 402a-n or emitted through optical filters 411a-n can be tuned based on the articles or substances known to be present in the detection environment. For example, at least one light source 402a-n in conjunction with optical filter 411a-n can be matched to correspond to a known absorption wavelength of the substance 460, thereby maximizing emission from substance 460. Additionally, wavelengths used by the light sources 402a-n can be selected to minimize emission from objects that are known to be present and do not need to be detected, for example, a diaper or an infant's skin.

In other cases, ranges of wavelengths can also be selected to maximize emission from undesired objects (e.g., an article or diaper) and to minimize emission from the substance to be detected. This approach provides a reference for the amount of undesired fluorophores present. The reference can then be used to adjust a measurement that maximizes a fluorescence of the substance based on the amount of interfering undesired fluorophores. For example, two ranges of emission wavelengths can be detected, one that includes a peak emission of the substance to be detected (e.g., in the example of FIG. 3, 630 nm or 700 nm) and one at an emission trough (e.g., considering FIG. 3, 600 nm or 680 nm). In this approach, the emission when stimulated at the trough level serves as a reference of the other fluorophores (e.g., article 450) in the area and emission when stimulated at the peak shows how much of substance 460 has caused a deviation from that reference.

Each photodetector 404a-n can include an optical filter 413a-n. Optical filters 413a-n remove certain wavelengths of light, thereby restricting the measured light at the photodetector 404a-n to a desired wavelength (e.g., the emission wavelength of substance 460). Each optical filter 413a-n is connected to a waveguide 414a-n. The waveguides direct the light received from the article 450 and other substances from receiving points, e.g., on the exterior of a sensing device. Waveguides 412a-n and 414a-n are optional; in some cases, waveguides may not be needed. In other cases, the functionality of waveguides 412a-n and 414a-n can be combined. For example, a particular waveguide can alternatively be exiting the article or measuring the returned light.

In an example, detection application 410 causes light source 402a and optical filter 411a to emit light at 430 nm. The light 440 is transmitted through waveguide 412a to article 450. Some of light 440 passes through article 450 as light 441. Some of light 440 is absorbed by article 450, some of which can cause a fluorescent emission. Continuing the example, light 441 is transmitted to substance 460 and causes substance 460 to fluoresce. Referring back to FIG. 3, substance 460 would fluoresce closely with the expected curves depicted in graph 310, with a higher amplitude peak of emitted light at 630 nm (marked as 311 on graph 310) and a lower amplitude peak of light at 700 nm (marked as 312 on graph 310).

As discussed, article 450 can also fluoresce, which can be measured by detection application 410. Detection application 410 can determine a presence or amount of substance 460 based on a relative intensity of a contribution of fluorescence from article 450 to a relative intensity of the fluorescence of substance 460.

Moreover, in some cases, substance 460 can absorb some of the fluorescence of article 450. For example, bodily exudate is initially on the inside surface and then is gradually absorbed into the absorbent article. When partially or wholly absorbed, the bodily exudate can potentially block some of the excitation light from reaching any fluorescent parts or layers of the absorbent article. A ratio of an amount of returned light at a first range of wavelengths versus an amount of returned light at a second range of wavelengths can therefore change based on how much of the bodily exudate has been absorbed into the article. In some cases, a higher concentration of substance, e.g., porphyrin, can cause an increase in returned light intensity relative to the returned light intensity caused by the article alone. This change can be detected by detection application 410.

Continuing the example, some of light 441 is passed through substance 460, as light 442, to skin 470, or passes around substance 460 (which may not be uniform in density or present in all areas). Light 446 is a combination of light that originates from skin 470, either as reflection or fluorescence from skin 470 and any ambient light. Light 447 represents light that is reflected or emitted from substance 460 and includes any contributions from light 446. Returned light 448, which is a combination of all reflected light from light 440 and other sources (including ambient light), and any emitted light from article 450, substance 460, or skin 470, is fed back to waveguides 414a and 414b.

The light from waveguides 414a-b passes to optical filter 413a, which is configured to remove components outside 630 nm, and to filter 413b, which removes components outside 700 nm. The returned light is measured by photodetectors 404a-b. Photodetector 404a measures an amplitude of received light at 700 nm. The detected amplitudes are provided to detection system 401.

Detection application 410 compares the received signals to thresholds. Based on the light at 630 nm being greater than a threshold in amplitude and/or the light at 700 nm being greater than a threshold in amplitude (which can be the same or a different threshold), detection application 410 determines whether substance 460 is present.

By adjusting the peaks of the wavelengths of the emitted light to match substance 460 and avoid other substances such as article 450 and skin 470, detection system 401 can detect a presence or absence of substance 460, even in the presence of other substances or objects such as skin 470, fluorescent or otherwise. For example, article 450 and/or skin 470 can have emission or fluorescent properties which can be similar to florescent properties of article 450. Color of skin 470 can vary by the wearer, therefore in some cases, detection system 401 can adjust or calibrate based on skin color.

Detecting a presence of a substance such as bodily exudate in an absorbent article can involve disambiguating effects measured from multiple different substances, each of which can have overlapping or additive characteristics. For example, diapers can auto-fluoresce due to one or more substances therein. One example is an optical brightener present in some diapers. For example, Benetex® OB Plus, chemical name: 2,5-Thiophenediylbis(5-tert-butyl-1,3-benzoxazole) is a fluorophore.

Figure 5:
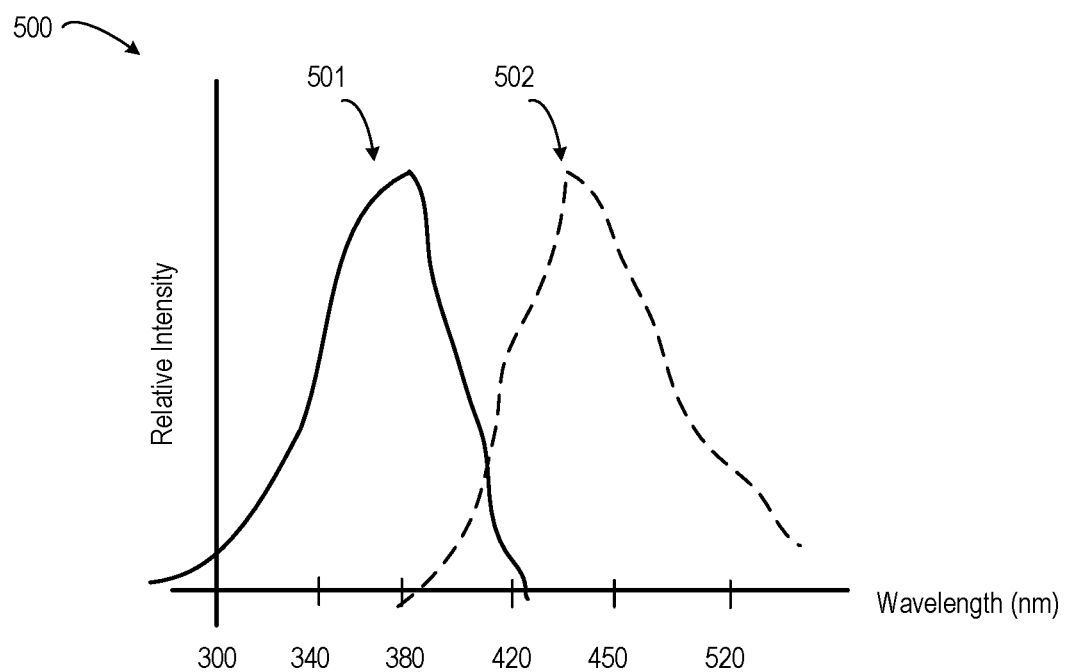
FIG. 5 depicts excitation and emission spectra of a substance commonly used in an absorbent article, according to an aspect of the present disclosure.

FIG. 5 depicts excitation and emission spectra of a substance commonly used in an absorbent article, according to an aspect of the present disclosure. Graph 500 depicts the abortion and emission spectra of Benetex® OB Plus. As can be seen, graph 501, which represents the absorption spectra, shows a maximum absorption wavelength of approximately 375 nm. Graph 502, which represents the emission spectra, illustrates a maximum fluorescence of 435 nm.

By carefully selecting the appropriate ranges of wavelengths of emitted light, any auto-fluorescence from a diaper can be minimized, while auto-fluorescence from bodily exudate maximized. Further, a diaper can absorb light and can absorb light at different amounts for at different wavelengths. Consequently, an amount of light that reaches the bodily exudate can be reduced, resulting in lower, or almost zero fluorescence. In these cases, a measure of emitted light after stimulation can be considered a reference measurement of the fluorescence of another object, e.g., a diaper. In some aspects, longer wavelengths which can penetrate a diaper better can be included in the ranges of wavelengths that are emitted.

Figure 6:
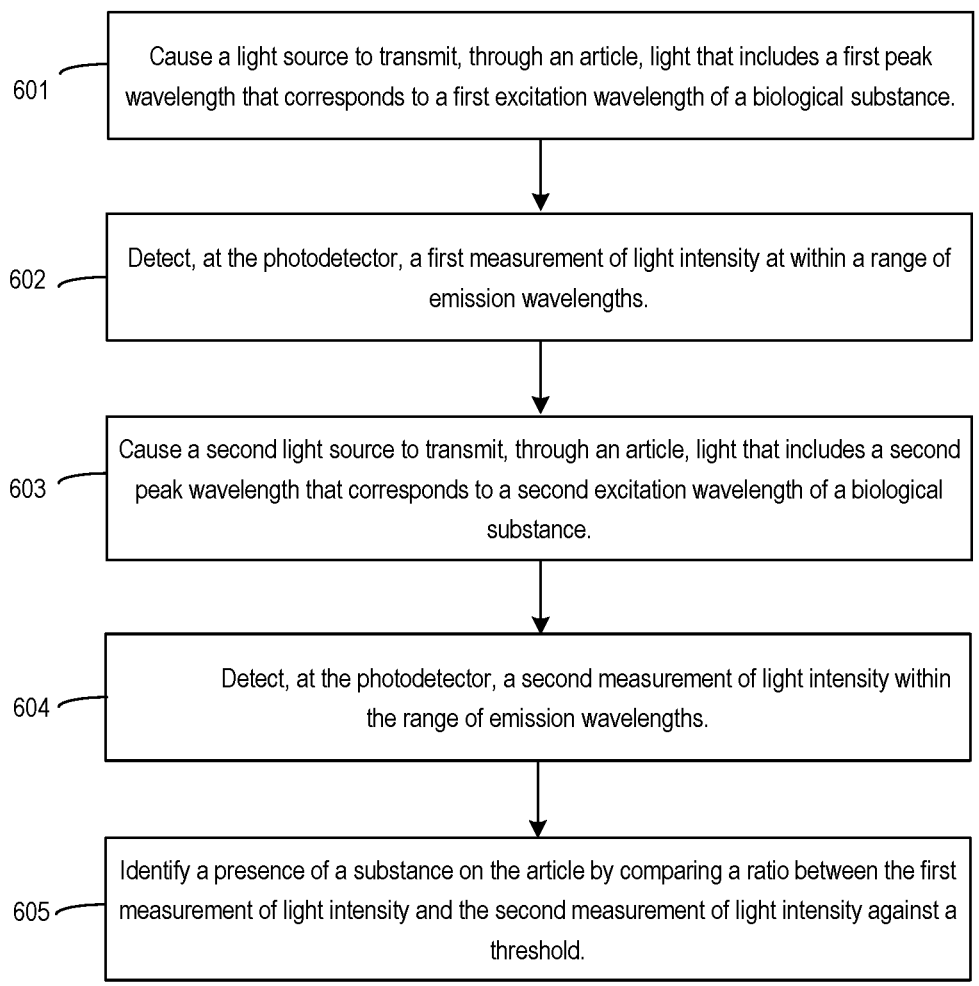
FIG. 6 illustrates an additional example of a process for detecting a presence of an auto-fluorescent biological substance by using a multiple-excitation and single emission approach, according to an aspect of the present disclosure.

FIG. 6 illustrates an additional example of a process 600 for detecting a presence of an auto-fluorescent biological substance by using a multiple-excitation and single emission approach, according to an aspect of the present disclosure. As further discussed, a multiple-excitation, single-emission approach is one of many approaches utilized by disclosed systems. With the multiple-excitation, single-emission approach, process 600 identifies a first amount of light emitted at a specific range of wavelengths when the substance is stimulated by light that includes a first excitation wavelength. Process 600 further identifies a second amount of light emitted at a second specific range of wavelengths when the substance is stimulated by light including a second peak wavelength. In some cases, the operations performed in process 200 can be combined with those operations in process 600.

Process 600 is discussed with respect to a Porphyrin, the curves for which are illustrated in FIG. 3. But process 600 can be used to detect other substances by adjusting the peak wavelength(s) of the light sources and the emission wavelength range(s).

At block 601, process 600 involves causing a light source to transmit, through an article, light that includes a first peak wavelength that corresponds to a first excitation wavelength of a biological substance. For example, detection application 410 can cause light source 402a and optical filter 411a to transmit light at 430 nm. As can be seen in FIG. 3, 430 nm corresponds to peak 301 on graph 300. Accordingly, causing light to be emitted at 430 nm can stimulate the substance to fluoresce. However, in some cases, light at 430 nm may not pass through the article, meaning that any substance therein will not be excited. Therefore, any measured light caused in response to the 430 nm excitation may solely be due to fluorescence of the article itself. In this case, therefore, the returned light represents a measure of the fluorescence of the article, which can be used as a baseline measurement.

Process 600 can also include ambient light detection and compensation. For example, prior to block 602, process 600 can involve detecting a contribution of ambient light, for example, with all light sources deactivated and quantifying the contribution.

At block 602, process 600 involves detecting a first measurement of light intensity within a range of emission wavelengths. Detection application 410 receives, from photodetector 404b, a first measure of light at 600 nm. Detection application 410 can wait for a small time (e.g., on the order of nanoseconds) for residual fluorescent effects to diminish. Accordingly, block 602 is executed after block 601. At block 602, process 600 also involves removing an ambient light measurement from the first measurement.

At block 603, process 600 involves causing a second light source to transmit, through an article, light that includes a second peak wavelength that corresponds to a second excitation wavelength of the biological substance. Detection application 410 causes light source 402b and optical filter 411b to transmit light at 510 nm, which is expected to be absorbed by the substance (see graph 300).

Process 600 can also include ambient light detection and compensation. For example, prior to block 604, process 600 can involve detecting a contribution of ambient light, for example, with all light sources deactivated and quantifying the contribution.

At block 604, process 600 involves detecting, at the photodetector, a second measurement of light intensity at a second emission wavelength. Detection application 410 receives, from photodetector 404b, a second measure of light at 600 nm. At block 604, process 600 also involves removing an ambient light measurement from the second measurement.

At block 605, process 600 involves identifying a presence of a substance on the article by comparing a ratio between the first measurement of light intensity and the second measurement of light intensity against a threshold. Detection application 410 computes a ratio of the first measure to the second measure.

By using multiple wavelengths and deriving ratios of amplitudes of light at the different wavelengths relative to a baseline, detection system 401 can disambiguate contributions in returned light measured at photodetectors 404a-n caused by, or are attributable to, substance 460 from contributions that are caused by, or attributed to, other articles and detect a presence of substance 460 even when the wearer of an article is moving. For example, detection application 410 can compare a ratio of light intensity emitted at 700 nm when the substance is excited at 610 nm to a measure of light intensity at 700 nm when the substance is excited at 430 nm, with a predefined, or calibrated ratio established as a baseline when no substance 460 is known to be present.

Further, a ratio can ensure that as sensors move, or move further away from the diaper, detection can still occur. For example, while the intensity changes, the ratio between the two emission wavelengths remains similar, thereby enabling the detection of the auto-fluorescence of the bodily exudate.

Returning to the example, detection application 410 determines a ratio of light emitted at 700 nm when excited at 610 nm to light emitted at 600-700 nm when excited at 430 nm of 5:1. Detection application 410 compares the ratio to a baseline ratio, when no substance 460 is present, of 1:1. Based on the detected ratio being greater, the detection application 410 determines that the substance 460 is present.

Exemplary Computing Systems

Figure 7:
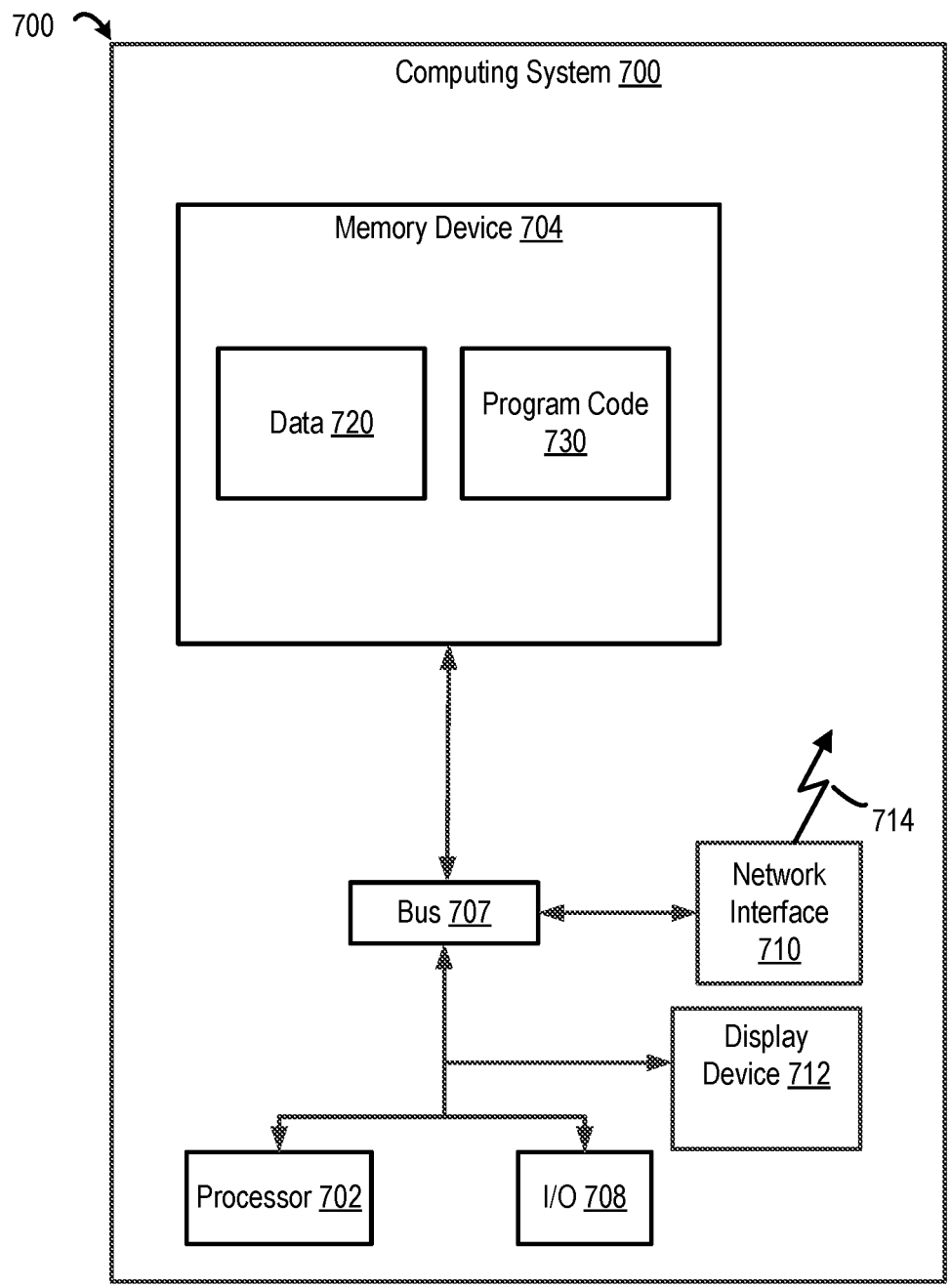
FIG. 7 is a diagram depicting an exemplary computing system for implementing functions relating to detecting a presence of a biological substance, according to an embodiment of the present disclosure.

FIG. 7 is a diagram depicting an exemplary computing system for implementing functions relating to detecting a presence of a biological substance, according to an embodiment of the present disclosure. FIG. 7 depicts computing device 700, which is an example of detection system 101. Any suitable computing system may be used for performing the operations described herein. The depicted example of a computing device 700, includes a processor 702 communicatively coupled to one or more memory devices 704. The processor 702 executes computer-executable program code 730 stored in a memory device 704, accesses data 720 stored in the memory device 704, or both. Program code 730 and/or data 720 can be from detection application 110 or 410.

Examples of the processor 702 include a microprocessor, an application-specific integrated circuit ("ASIC"), a field-programmable gate array ("FPGA"), or any other suitable processing device. The processor 702 can include any number of processing devices or cores, including a single processing device. The functionality of the computing device may be implemented in hardware, software, firmware, or a combination thereof.

The memory device 704 includes any suitable non-transitory, computer-readable medium for storing data, program code, or both. Memory device 704 can include data, program code, or both, for detection application 110 or 410. A computer-readable medium can include any electronic, optical, magnetic, or other storage device capable of providing a processor with computer-readable instructions or other program code. Non-limiting examples of a computer-readable medium include a flash memory, a ROM, a RAM, an ASIC, or any other medium from which a processing device can read instructions. The instructions may include processor-specific instructions generated by a compiler or an interpreter from code written in any suitable computer-programming language, including, for example, C, C++, C #, Visual Basic, Java, or scripting language.

The computing device 700 may also include a number of external or internal devices, such as input or output devices. For example, the computing device 700 is shown with one or more input/output ("I/O") interfaces 707. An I/O interface 707 can receive input from input devices or provide output to output devices. One or more busses 707 are also included in the computing device 700. The bus 707 communicatively couples one or more components of a respective one of the computing device 700.

The computing device 700 executes program code 730 that configures the processor 702 to perform one or more of the operations described herein. For example, the program code 730 causes the processor to perform the operations described in FIG. 2 or 6.

The computing device 700 also includes a network interface device 710. The network interface device 710 includes any device or group of devices suitable for establishing a wired or wireless data connection to one or more data networks. The network interface device 710 may be a wireless device and have an antenna 714. The computing device 700 can communicate with one or more other computing devices implementing the computing device or other functionality via a data network using the network interface device 710.

The computing device 700 can also include a display device 712. Display device 712 can be a LCD, LED, touch-screen or other device operable to display information about the computing device 700. For example, information could include an operational status of the computing device, network status, etc.

General Considerations

While the present subject matter has been described in detail with respect to specific aspects thereof, it will be appreciated that those skilled in the art, upon attaining an understanding of the foregoing may readily produce alterations to, variations of, and equivalents to such aspects. Accordingly, it should be understood that the present disclosure has been presented for purposes of example rather than limitation, and does not preclude inclusion of such modifications, variations, or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification, discussions utilizing terms such as "processing," "computing," "calculating," "determining," and "identifying," or the like, refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computer systems accessing stored software that programs or configures the computing system from a general-purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

Aspects of the methods disclosed herein may be performed in the operation of such computing devices. The order of the blocks presented in the examples above can be varied—for example, blocks can be re-ordered, combined, or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, or steps. Thus, such conditional language is not generally intended to imply that features, elements or steps are in any way required for one or more examples or that one or more examples necessarily include logic for deciding, with or without author input or prompting, whether these features, elements or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

That which is claimed is:

1. A method comprising:
    causing, at a first time, a first light source to transmit, through an article, light that includes a first peak wavelength that corresponds to a first excitation wavelength of a biological substance, the biological substance comprising multiple excitation wavelengths;
    detecting a first measurement of light intensity within a first range of emission wavelengths of the biological substance;
    causing, at a second time, a second light source to transmit, through the article, light that includes a second peak wavelength that corresponds to a second excitation wavelength of the biological substance, wherein the first peak wavelength is different from the second peak wavelength;
    detecting a second measurement of light intensity within a second range of emission wavelengths of the biological substance; and
    responsive to comparing a ratio of the first measurement of light intensity and the second measurement of light intensity against a threshold, identifying a presence of the biological substance on the article.

2. The method of claim 1, wherein the first excitation wavelength is different from the second peak wavelength.

3. The method of claim 1, wherein identifying the presence of the biological substance further comprises comparing the first measurement of light intensity to a first threshold and comparing the second measurement of light intensity to a second threshold.

4. The method of claim 1, wherein identifying the presence of the biological substance further comprises calculating an additional ratio of the first measurement of light intensity to the second measurement of light intensity and comparing the additional ratio to an additional threshold.

5. The method of claim 1, wherein the first excitation wavelength and the second excitation wavelength are between 405 and 720 nm.

6. The method of claim 1, wherein the first range of emission wavelengths does not overlap with the second range of emission wavelengths, the first range of emission wavelengths is between 600-720 nm, and the second range of emission wavelengths is between 600-720 nm.

7. The method of claim 1, wherein the first excitation wavelength is between 380 to 740 nm, the second excitation wavelength is between 380 to 740 nm, and the first range of emission wavelengths and the second range of emission wavelengths are between 600 and 720 nm.

8. The method of claim 1, wherein the first range of emission wavelengths comprises at least one wavelength in common with the second range of emission wavelengths.

9. The method of claim 1, further comprising:
obtaining a baseline measurement of light intensity, the baseline measurement of light intensity comprising a contribution of ambient light; and
removing, from the first measurement of light intensity and from the second measurement of light intensity, the baseline measurement of light intensity.

10. A method comprising:
causing a light source to transmit, through an article, light that includes a peak excitation wavelength that corresponds to an excitation wavelength of a biological substance;
detecting a measurement of light intensity within a first range of emission wavelengths of the biological substance, wherein the biological substance has multiple emission wavelengths and wherein the first range of emission wavelengths has a first peak emission wavelength;
detecting an additional measurement of light intensity within a second range of emission wavelengths of the biological substance, wherein the second range of emission wavelengths has a second peak emission wavelength that is different than the first peak emission wavelength; and
responsive to comparing the measurement of light intensity against a threshold and comparing the additional measurement of light intensity against an additional threshold, identifying a presence of the biological substance on the article.

11. The method of claim 10, wherein the peak excitation wavelength is between 405 and 650 nm, the first range of emission wavelengths is either 620 to 640 nm or 650 to 710 nm, and the second range of emission wavelengths is either 620 to 640 nm or 650 to 710 nm.

12. The method of claim 10, wherein the biological substance is a porphyrin.

13. A system comprising:
a first light source configured to emit light that includes a first peak wavelength that corresponds to a first excitation wavelength of a biological substance;
a second light source configured to emit light that includes a second peak wavelength that corresponds to a second excitation wavelength of the biological substance, wherein the first peak wavelength is different from the second peak wavelength;
a photodetector configured to measure an intensity of light within a range of emission wavelengths of the biological substance; and
a processor configured to perform operations comprising:
cause the first light source to transmit light through an article at a first time;
detect a first measurement of light intensity at the photodetector at a second time that is different from the first time;
cause the second light source to transmit light through the article at a third time different from the second time;
detect a second measurement of light intensity at the photodetector at a fourth time different from the third time; and
responsive to comparing a ratio of the first measurement of light intensity and the second measurement of light intensity against a threshold, identifying a presence of the biological substance on the article.

14. The system of claim 13, further comprising:
a first light filter coupled to the first light source;
a second light filter coupled to the second light source; and
a third light filter coupled to the photodetector.

15. The system of claim 13, wherein the first peak wavelength and the second peak wavelength are between 380 and 720 nm.

16. The system of claim 13, wherein the range of emission wavelengths is either 620 to 640 nm or 650 to 710 nm.

17. The system of claim 13, wherein the first excitation wavelength and the second excitation wavelength are between 380 to 740 nm and the range of emission wavelengths 600 to 720 nm.

18. The system of claim 13, wherein identifying the presence of the biological substance further comprises:
comparing the first measurement of light intensity to a first threshold;
comparing the second measurement of light intensity to a second threshold; and
calculating an additional ratio of the first measurement of light intensity to the second measurement of light intensity and comparing the ratio to a third threshold.

19. The system of claim 13, wherein the operations further comprise:
obtaining, from the photodetector, a baseline measurement of light intensity, the baseline measurement of light intensity comprising a contribution of ambient light; and
removing, from the first measurement of light intensity and from the second measurement of light intensity, the baseline measurement of light intensity.

20. The system of claim 13, wherein the second measurement of light intensity and the first measurement of light intensity represent non-overlapping ranges of wavelengths.

21. The method of claim 10, wherein the first range of emission wavelengths and second range of emission wavelengths are either 620 to 640 nm or 650 to 710 nm.

* * * * *